United States Patent [19]

Cewers et al.

[11] Patent Number: 4,623,331
[45] Date of Patent: Nov. 18, 1986

[54] APPARATUS FOR THE REGISTRATION OF DROPS IN AN INFUSION DEVICE

[75] Inventors: Göeran Cewers, Lund; Sven-Gunnar Olsson, Soedra Sandby, both of Sweden

[73] Assignees: Siemens Aktiengesellschaft, Berlin & Munich, Fed. Rep. of Germany; Siemens Elema AB, Solna, Sweden

[21] Appl. No.: 678,675

[22] Filed: Dec. 6, 1984

[30] Foreign Application Priority Data

Dec. 9, 1983 [DE] Fed. Rep. of Germany ....... 3344632

[51] Int. Cl.⁴ ............................................. A61M 5/00
[52] U.S. Cl. .................................... 604/65; 604/253
[58] Field of Search .............................. 128/DIG. 13; 604/65-67, 251, 253; 73/861.41; 222/420, 422; 250/560

[56] References Cited

U.S. PATENT DOCUMENTS

| | | | |
|---|---|---|---|
| 2,880,764 | 4/1959 | Pelavis | 73/861.41 X |
| 3,500,366 | 3/1970 | Chesney et al. | 604/253 X |
| 3,545,271 | 12/1970 | Amir et al. | 604/253 X |
| 3,700,904 | 10/1972 | Stobble et al. | 604/65 X |
| 4,328,801 | 5/1982 | Marx et al. | 604/65 |
| 4,346,606 | 8/1982 | Cannon et al. | 604/253 X |
| 4,432,761 | 2/1984 | Dawe | 604/253 |

Primary Examiner—Edward M. Coven
Attorney, Agent, or Firm—Hill, Van Santen, Steadman & Simpson

[57] ABSTRACT

An apparatus for the registration of drops in an infusion device has a drip chamber from which fluid is supplied from a reservoir through a tube to a patient, with a drop sensor disposed in the region of the drip chamber. The drop sensor is divided into at least two levels, each level having a processing channel allocated thereto including an amplifier, a comparator and a memory. The outputs of each channel are supplied to a logic unit. As long as signals are supplied by each channel to the logic unit, normal and proper operation is assumed, however, a discriminator unit triggers a fault display or an alarm when a signal from only one channel is present within a predetermined time.

22 Claims, 3 Drawing Figures

APPARATUS FOR THE REGISTRATION OF DROPS IN AN INFUSION DEVICE

BACKGROUND OF THE INVENTION

1. Field of the Invention

The present invention relates to devices for the registration of drops in infusion devices, and in particular to such an apparatus wherein the infusion device includes a drip chamber connected to a reservoir for supplying infusion fluid to a patient via a tube.

2. Description of the Prior Art

Various factors complicate registration of a drop in a drip chamber when optical measuring methods are utilized in an infusion device of the type having a reservoir containing infusion fluid which is supplied to the drip chamber, the fluid being then supplied from the drip chamber to the patient via a tube. Optical measuring methods employing a light source and a light sensor may give false data when the transparency of the wall of the drip chamber becomes deteriorated such as, for example, by fluid vapor precipitation thereon, splattering resulting from drops incident on the fluid surface within the chamber, or jolts to the drip chamber. Splatters or a rippled fluid surface caused by vibrations can additionally cause incorrect drop indications. Vibrations or tilting of the drip chamber may mean that the drop descends obliquely through the chamber. It is also possible for the electronics employed for processing the signals or the light source or the light sensor, to deteriorate over time in terms of electrical properties, and thereby render the registration less certain.

One apparatus attempting to avoid such errors in drop registration is disclosed in German OS No. 28 30 512, wherein a plurality of light sources and photodetectors are disposed on the circumference of the drop chamber in a plane perpendicular to the drop direction. This apparatus still provides reliable registration data even if the drip chamber is unfavorably tilted.

Another apparatus is known from U.S. Pat. No. 4,038,981 wherein one light source and two phototransistors are disposed in one plane. The sensitivity of the drop sensor and tilted attitudes of the chamber are taken into consideration by this device. A fluid line is released by a clock generator and an error element is set at the same time, the error element triggering a fault indication and/or an alarm when a reset signal is not received from the drop detector within a predetermined time. In this apparatus, a drop must be released each time by means of an actuating valve, the occurrence of the drop being documented by the drop sensor, whereupon the valve is then closed. The phototransistors are connected in parallel, with their collector voltages switched to a pulse shaver by an ac voltage signal. The circuit is thus balanced even when less light is incident on the phototransistors. When, however, the sensitivity of the apparatus becomes so poor for any reason such that drop detection is uncertain, this may result in serious errors. It may occur, for example, that only every other drop is registered and thus an undesirably large amount of infusion fluid is administered to the patient. Additionally, a measurement of blood pressure may, for example, delay the drop initiation and trigger an alarm by the error stage when no such alarm is actually warranted.

SUMMARY OF THE INVENTION

It is an object of the present invention to provide an apparatus for the registration cf drops in an infusion device wherein errors in drop registration are avoided in a simple manner.

It is a further object of the present invention to provide such an apparatus which does not require coupling to a valve means for releasing the drops.

It is a further object of the present invention to provide such an apparatus wherein a simple function check of the drop sensor can be undertaken.

The above objects are inventively achieved in a drop registration sensor for use in an infusion device of the type described above wherein the drop sensor is divided into at least two planes, each of which has its own detector circuit channel including an amplifier, a comparator and a storage element. The outputs of each channel are supplied to a common logic unit which can activate a drop display given the presence of a signal from at least one channel, but also from both channels. The output signals of each channel are also supplied to a discriminator unit which additionally receives a signal from the logic unit. The discriminator unit provides a fault indication when no signal indicating that all levels have detected a drop is received from the logic unit within a specified period of time after the appearance of a first channel signal. Thus if only one signal is received from one of the channels within a specified period of time, a fault indication is activated. The discriminator unit thus indicates when the detection of a drop by the drop sensor and the following detector channels becomes uncertain for any reason whatsoever.

In a preferred embodiment, the ac voltage components of the output signals of each of the channels, after amplification under certain conditions, are connected to a pulse shaper or comparator. A drop registration that is independent of the transparency of the drip chamber is thus possible. In contrast to conventional devices, the drop sensor having at least two sensing planes, that is, sensing the presence or absence of a drop at at least two levels, permits the functional reliability of the overall apparatus to be easily checked. The apparatus may be operated such that each sensing plane has a different sensitivity. Because a fault signal is triggered when all planes or levels have not detected a drop within a prescribed time, a fault or warning signal can be generated in time within the decisive transition region during which drop detection is uncertain.

In a further embodiment of the invention, the energy consumption of the device may be reduced wherein the light sources for each sensing level as well as the light sensors are clocked. In order to assure a reliable further processing of the pulsed signals, a sample-and-hold circuit may be provided within the detector channels, the sample-and-hold circuit being clock synchronously with the light source and the light sensors.

In order to quickly indicate a faulty positioning of the drip chamber in a simple manner, a further embodiment of the invention includes a magnet provided in the drip chamber, and a hall element contained, for example, within the bracket supporting the drip chamber. The output signal of the hall element is supplied to a memory or storage flip flop. When the drip chamber is not in its prescribed position, the distance between the magnet and the hall element is enlarged and an output signal which sets the storage flip flop and initiates a counter is supplied by the hall element. Because the other storage flip flops in the detector channels are not set, a fault signal is generated after the prescribed counter time.

The hall element may be clocked in order to reduce energy consumption.

DESCRIPTION OF THE PREFERRED EMBODIMENTS

Figure 1:
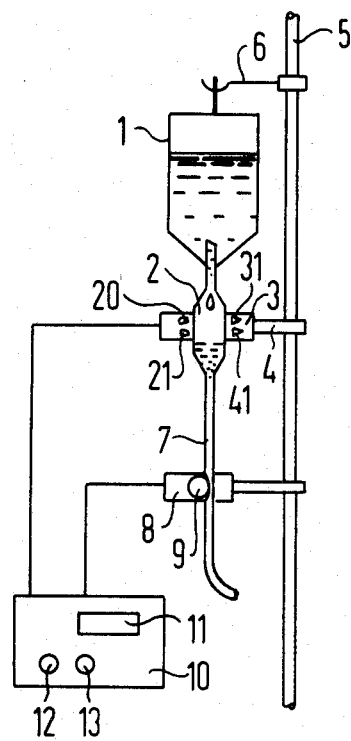
FIG. 1 is a side view of an infusion device including a drop registration apparatus constructed in accordance with the principles of the present invention.

An infusion device is shown in FIG. 1 including a bottle 1 containing infusion liquid connected to a drip chamber 2 in a standard manner. The drip chamber 2 consists of transparent material so that a drop event can be observed. The drip chamber 2 is secured in a holder 3 which is connected via a bracket 4 to a stand 5. A hanger 6, also connected to the stand 5, supports the bottle 1.

A tube 7 through which the infusion liquid is supplied to a patient is connected to the drip chamber 2. The cross-section of the tube 7 and thus the amount of liquid flow therethrough is regulated by a clamp device 8 having an eccentric cam 9 thereon, which can also be connected to the stand 5.

The device also has a control and display unit 10 connected both to the clamp device 8 and to the drop sensor, which is contained in the holder 3. The desired flow amount, that is, the number of drops or the total amount of infusion fluid to be administered, can be set and regulated by the display and control device 10. The momentary drip rate or the amount of infusion fluid already administered or similar data can be represented on a visual display 11. The individual drops can be optically displayed, for example, by means of a lamp 12 or light emitting diodes. A further optical display 13 may, for example, indicate the occurrence of a fault. As is known, an audio alarm may also be triggered in the event of a fault and/or fluid delivery can be interrupted by means of the clamp device 8.

As stated above, the drop sensor constructed in accordance with the principles of the present invention is contained within the holder 3, and includes two light sources 20 and 21 and two light sensors 31 and 41, in addition to a hall element, not shown in FIG. 1. The drop chamber 2 is also equipped with a magnet (not shown) in the region of the hall element. The two light sources 20 and 21 in combination with the sensors 31 and 41 provide two sensing planes for detecting drops within the drip chamber 2. As will be apparent from the discussion below, the inventive concept disclosed and claimed herein is not limited to an apparatus having only two sensing planes; any number of sensing planes may be employed to increase the sensitivity of the device as needed.

Figure 2:
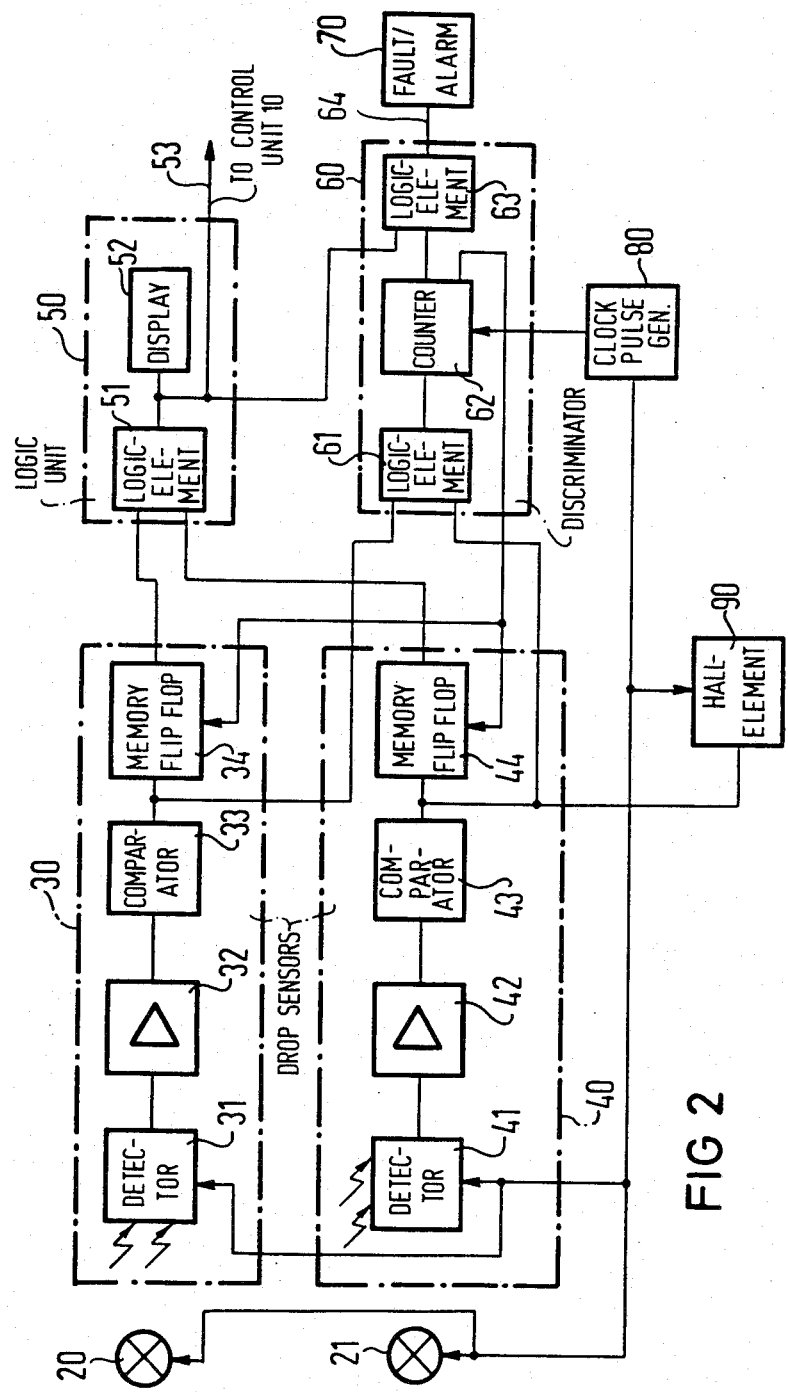
FIG. 2 is a simplified block diagram of a drop registration device constructed in accordance with the principles of the present invention.

A simplified block diagram of the processing circuitry for the inventive drop registration apparatus is shown in FIG. 2. Each light source 20 and 21 has a drop sensor channel allocated thereto, respectively indicated 30 and 40 in FIG. 2. The light sources 20 and 21 may be individual light emitting diodes, however, it is also possible to provide only a single light source and to expand the light beam radiating therefrom with the assistance of lenses such that a larger region of the drip chamber 2 is illuminated.

Each drop sensor channel 30 and 40 contains respective light detectors 31 and 41, such as photodiodes, respective amplifiers 32 and 42, respective comparitors 33 and 43, and respective memories 34 and 44, which may be storage flip flops. The outputs of the memories 34 and 44 are supplied to a logic unit 50, which includes a logic element 51 and a display 52. The output of the logic unit 50 is supplied via an output line 53 to the control and display device 10 for regulating the drop rate.

The output signals of the two comparitors 33 and 43 are each supplied to a logic element 61 of a discriminator unit 60. The output signal of the logic element 61 resets and starts a counter 62. The discriminator 60 also includes a further logic element 63, to which the counter output and the output of the logic unit 50 are supplied. The output of the logic element 63 is supplied via an output line 64 to a fault or alarm means 70.

The counter 62 of the discriminator unit 60 is supplied with clock pulses from a clock pulse generator 80. The aforementioned hall element 90 is also shown in FIG. 2, the output thereof being connected to the memory 44. The circuit shown in FIG. 2 may be continuously operated, however, in order to advantageously reduce the power consumption, which is particularly beneficial for ambulatory operation of the apparatus, can be achieved if the light sources 20 and 21, the light detectors 31 and 41, and the hall element 90 are all clocked by means of the clock pulse generator 80.

As stated above, each of the drop sensors 30 and 40 constitute a separate detector channel allocated to one of the light sources 20 and 21. The two channels may have adjustable sensitivities, which may be set to different levels with respect to the other channel. Such adjustment can be undertaken by means of the comparitors 33 and 43. The output signals of the two drop sensors 30 and 40 are supplied to the logic unit 50 in which a determination is made by the logic element 51 as to whether both drop sensors have detected a drop. If this is so, the display 52 is activated by the output signal of the logic element 51. The memories 34 and 44 ensure that a drop detected in chronological succession by the drop sensors 30 and 40 will activate the logic element 51 such that a drop indication in fact occurs.

The output signals of the comparitors 33 and 43 are also supplied to the discriminator unit 60 through the logic element 61. The counter 62 is already reset and started by the occurrence of one discriminator output signal. When a specific count has been reached, the counter 62 supplies a signal to the logic element 63. When the second drop sensor has also detected a drop in the meantime, such that a change in the output signal of the logic element 51 has occurred, the fault or alarm device 70 is not activated.

Regardless of whether a drop has been detected by both drop sensors 30 and 40, or by only one of those sensors, the counter 62 continues to count to a further counter reading, at which point a signal is supplied to set the two memories 34 and 44 to their initial state. Simple storage flip flops can be employed as the memories 34 and 44. The purpose of the discriminator unit 60 is thus to generate a warning signal when one of the drop sensors 30 or 40 has not detected a drop due, for example, to fog in the drip chamber 2, splattering against the wall of the drip chamber 2, or due to any other type of disruption. If the two drop sensors 30 and 40 are set to different sensitivites, a fault or alarm signal is triggered after a certain limit value, for example given a slowly increasing contamination of the wall of the drip chamber 2. One drop sensor will still always function so that a function check can be reliably executed.

Figure 3:
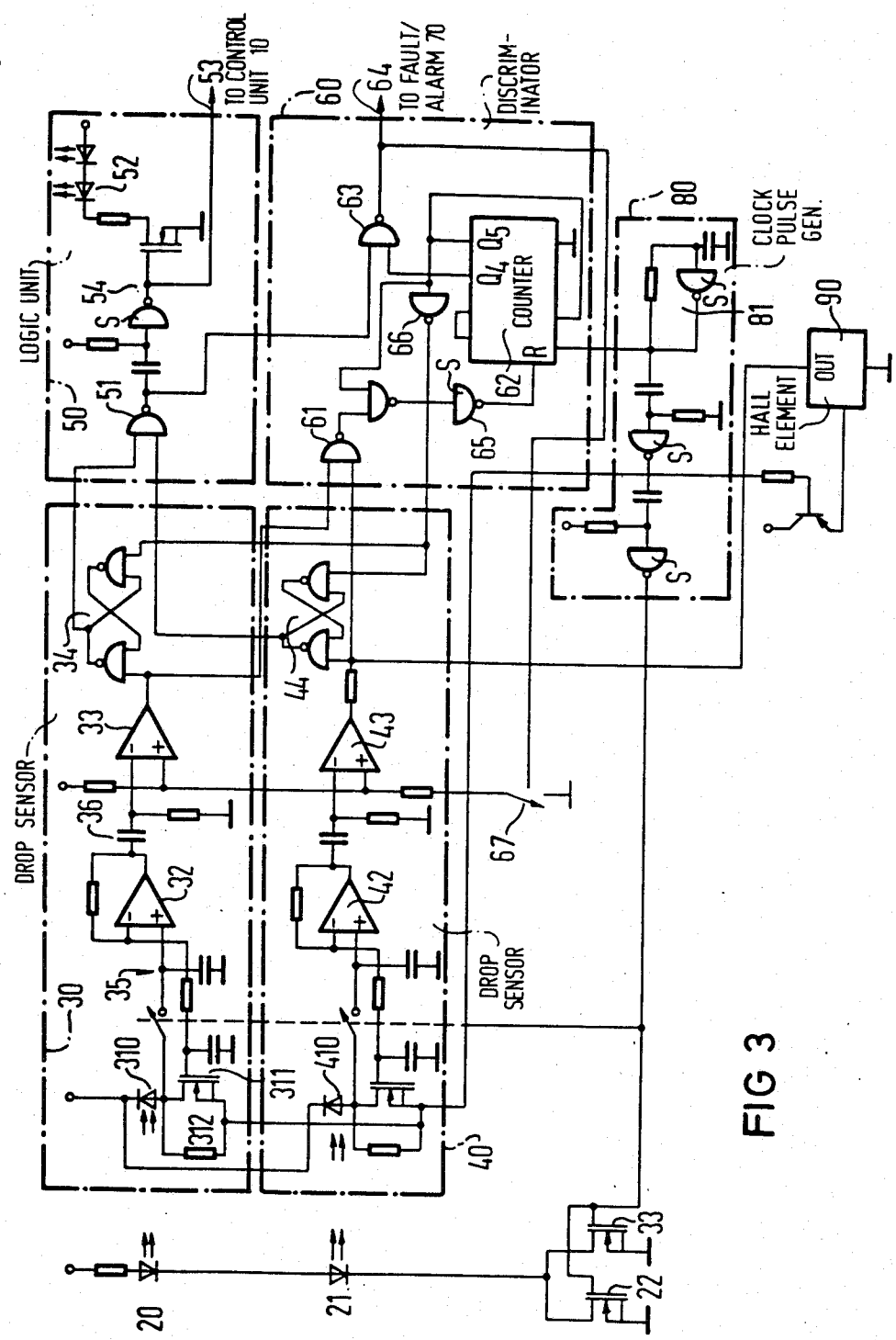
FIG. 3 is a schematic circuit diagram showing an embodiment of the apparatus shown in FIG. 2.

A more detailed circuit embodiment of the apparatus shown in FIG. 2 is shown in FIG. 3, with identical elements being referenced with the same reference characters.

In this embodiment, the light sources 20 and 21 may be infrared light emitting diodes clocked, for example, by switching transistors 22 and 23 at a frequency of approximately 200 Hz and a pulse length of 1.5 microseconds. The clock frequency is obtained by a constantly oscillating oscillator 81 and a series of pulse shaping components S included in the clock pulse generator 80.

The drop sensors 30 and 40, as explained above, are identical except for possibly having different sensitivities, therefore the circuit format and operation of only the drop sensor 30 will be described, it being understood that the operation of the drop sensor 40 is the same.

An infrared photodiode 310 serves as a light sensor (photodiode 410 in sensor 40), forming a voltage divider in combination with a MOS transistor 311 and a resistor 312 and being clocked synchronously with the light source 20. The synchronous clocking is undertaken by the generator 80. The clock frequency is therefore the same, however the duration of the clock pulses supplied to the light sensor 310 may be longer so that reception of the emitted light pulses is assured. The clock pulses supplied to the photodiode 310 may have a length of, for example, 10 microseconds. The output of the voltage divider is supplied to the amplifier 32 via a sample-and-hold element 35. The processing of the received signals which follows is thus independent of their time duration. The feedback loop of the amplifier 32 is also connected to the gate of the transistor 311 in the voltage divider, thus effecting an automatic offset adjustment of the voltage division.

A capacitor 36 is utilized to supply the ac component of the output signal of the amplifier 32 to a comparitor 33 which may, for example, detect the positive edges of the signal. The output signal of the comparitor 33 is supplied to the memory flip flop 34, which is thereby set. The flip flop 34 is reset by the discriminator unit 60. As soon as a comparitor signal is present, and thus one (or both) of the storage flip flops 34 and 44 is set, the counter 62 of the discriminator unit 60 is reset and started by the logic element 61 and a NAND gate 64 and, under certain conditions, by means of further logic or inverting elements. The pulses for the counter 62 are also supplied by the clock pulse generator 80. The counting frequency, as already mentioned, is approximately 200 Hz. When the counter 62 reaches a count of 16 clock pulses, which corresponds to approximately 80 milliseconds, a signal is supplied by the counter output $Q_4$ to the logic element 63, also a NAND gate, which emits a fault signal when both storage flip flops 34 and 44 have not been set, that is, a drop has not been detected by either drop sensors 30 and 40.

Regardless of whether a drop has been detected, the counter 62 continues to count a further 80 milliseconds and then stops and resets the two memory flip flops 34 and 44 via an inverter element 66. If a fault has occurred, that is, when the output of the NAND gate 63 has changed state, the comparison voltage at the comparitors 33 and 43 is changed by a switch 67 such that the comparitors cannot detect futher drops. This condition can be maintained until a final counter reading is reached, so that the fault signal is present for a sufficiently long time to reliably activate the necessary fault elements.

The output signals of both memories 34 and 44 are supplied to the logic element 51, also a NAND gate. When both memories are set, that is, when both drop sensors have detected a drop, the output status of the logic element 51 changes. This signal is supplied to the logic element 63 and also proceeds to a pulse generator 54 which activates the drop display 52, for example, light emitting diodes.

As mentioned above, a hall element 90 is utilized for indicating the proper positioning of the drip chamber 2 in the holder 3 of FIG. 1, the drip chamber 2 having a magnet secured thereto. It is also possible to secure the magnet to the holder 3 and the hall element to the drip chamber 2. The hall element 90 is clocked in order to further reduce power consumption. When the drip chamber 2 is removed from the holder 3, or when the drip chamber 2 is not in a prescribed position, the distance between the magnet and the hall element 90 changes, whereupon the hall element 90 generates an output signal which is supplied to one of the memories, such as memory 44, which is set by that signal. This automatically causes a fault signal at the output of the NAND gate 63. It is thus possible with very little additional circuit outlay to undertake a positional check of the drip chamber 2 in the holder 3, in addition to the function check of the apparatus for detecting the drops by use of the same circuitry.

The apparatus described above can document the occurrence of one drop within a total computational time of, in the above example, approximately 160 milliseconds. This has the advantage that splattering proceeding from this drop in the drop chamber 2, for example from the surface of the infusion liquid, cannot cause erroneous detectors within this time interval. The interval is, however, short enough to detect all drops given standard flow rates of the infusion fluid. If in an extreme case a higher drop frequency is required, the apparatus will detect, for example, every other drop. The function check of the apparatus, however, remains assured.

Although modifications and changes may be suggested by those skilled in the art it is the intention of the inventor to embody within the patent warranted hereon all changes and modifications as reasonably and properly come within the scope of his contribution to the art.

We claim as our invention:

1. A drop registration apparatus for use with an infusion device having an infusion fluid reservoir, a drip chamber, and a tube in fluid communication, said apparatus comprising:
   at least one light source;
   at least two light sensors disposed such that drops in said drip chamber fall in sequence between said light source and each of said light sensors;
   at least two detector channels respectively allocated to said light sensors, each detector channel independently generating a detector output signal when the light sensor allocated thereto senses a drop;
   a logic means having inputs connected to said detector channels for generating a logic output signal indicating proper operation of said infusion device when at least one of said detectors generates a detector output;

a discriminator means having inputs connected to said detector channels, said discriminator means generating a discriminator output signal if a detector output signal is not received from all detector channels within a first selected time period; and a fault/alarm means having an input connected to said discriminator means for generating a fault/alarm signal upon receipt of said discriminator output signal.

2. A drop registration apparatus as claimed in claim 1 wherein said detector channels have different sensitivities.

3. A drop registration apparatus as claimed in claim 1 wherein said light source consists of two light emitting diodes disposed in sequence in the direction of drip fall.

4. A drop registration apparatus as claimed in claim 1 further comprising a transistor connected to each of said light sensors, said transistors and light sensors forming respective voltage dividers.

5. A drop registration apparatus as claimed in claim 4 wherein each said detector channel includes an amplifier having an input connected to a tap of said voltage divider.

6. A drop registration apparatus as claimed in claim 5 wherein said amplifier has a feed back loop connected to a control input of said transistor.

7. A drop registration apparatus as claimed in claim 5 wherein the respective amplifiers in said detector channels have different sensitivities.

8. A drop registration apparatus as claimed in claim 5 wherein each detector channel further comprises a means for filtering out the dc component of the output of said amplifier, and a comparitor having an input to which the remaining ac component of said amplifier output is supplied, and having another input to which a comparison voltage is supplied.

9. A drop registration apparatus as claimed in claim 8 further comprising a means for inhibiting said comparitors upon the occurrence of a discriminator output signal.

10. A drop registration apparatus as claimed in claim 9 wherein said means for inhibiting is an electronic switch connected to said inputs of said comparitors to which said comparison voltage is supplied, said electronic switch interrupting supply of said comparison voltage to said inputs upon the occurrence of a discriminator output signal.

11. A drop registration apparatus as claimed in claim 8 wherein said comparison voltage is different for the respective comparitors in said detector channels.

12. A drop registration apparatus as claimed in claim 8 further comprising a means for adjusting said comparitor voltage.

13. A drop registration apparatus as claimed in claim 8 wherein each detector channel further comprises a storage flip flop having a set input connected to the output of said comparitor, a reset input, and an output connected to said logic means, and wherein said discriminator means further comprises a means connected to said reset input of each storage flip flop for resetting each flip flop after a second selected time period.

14. A drop registration apparatus as claimed in claim 13 further comprising a holder means for said drip chamber, said holder means having a hall element mounted therewith, and said drip chamber having a magnet attached thereto, said hall element having an output connected to a set input of one of said storage flip flops and supplying a signal to said one of said storage flip flops whenever the distance between said magnet and said hall element changes.

15. A drop registration apparatus as claimed in claim 13 wherein said logic unit includes a logic element having a plurality of inputs respectively connected to the outputs of said storage flips flops, said logic element changing state when at least one of said storage flip flops is set.

16. A drop registration apparatus as claimed in claim 13 further comprising a logic pulse generator means and a drop display means driven by said logic pulse generator, said logic pulse generator having an input connected to said logic element for enabling said logic pulse generator whenever one of said storage flip flops is set.

17. A drop registration apparatus as claimed in claim 16 wherein said discriminator means includes a clocked counter, said clocked counter having a reset input connected to the outputs of said comparitors such that said counter is reset and started by the occurrence of a signal at the output of one of said counters, said counter generating a first output signal after a selected counter reading corresponding to said first selected time period, and supplying a second output signal after a higher selected counter reading corresponding to said second time period, said discriminator unit further including a discriminator logic element having inputs respectively connected to said first counter output and the output of said logic element in said logic unit, said discriminator logic element generating said discriminator output signal, and said second output signal being supplied to said reset inputs of said storage flip flops.

18. A drop registration apparatus as claimed in claim 1 further comprising a clock pulse generator means for synchronously clocking said light source and said light sensors.

19. A drop registration apparatus as claimed in claim 18 wherein said clock pulse generator means is an oscillator, and wherein said oscillator is also connected to said counter for supplying a clock signal thereto.

20. A drop registration apparatus for use with an infusion device having an infusion fluid reservoir, a drip chamber, and a tube in sequential fluid communication, said apparatus comprising:

a sensor means dividing said drip chamber into at least two sensing planes;

detector means respectively independently allocated to each sensing plane for generating a signal when a drop is sensed in the plane allocated thereto;

means connected to said detector means for determining and indicating proper operation of said infusion device when a signal is generated by a detector means for at least one sensing plane; and means connected to said detector means for generating a fault signal when a drop has not been sensed in all sensing planes within a selected time period.

21. A drop registration apparatus as claimed in claim 20 wherein said sensing planes are non-intersecting.

22. A drop registration apparatus as claimed in claim 20 wherein said sensing planes are disposed substantially perpendicularly to a direction of fall of a drop in said drip chamber.

* * * * *